United States Patent [19]

Dahlbäck

[11] Patent Number: 5,443,960
[45] Date of Patent: Aug. 22, 1995

[54] METHOD FOR THE DIAGNOSIS OF BLOOD COAGULATION DISORDERS

[76] Inventor: Björn Dahlbäck, Plantskolevägen 10, S-216 21 Malmö, Sweden

[21] Appl. No.: 199,328
[22] PCT Filed: May 13, 1992
[86] PCT No.: PCT/SE92/00310
  § 371 Date: May 27, 1994
  § 102(e) Date: May 27, 1994
[87] PCT Pub. No.: WO93/10261
  PCT Pub. Date: May 27, 1993

[30] Foreign Application Priority Data

Nov. 13, 1991 [SE] Sweden .................. 9103332-4

[51] Int. Cl.⁶ .................... C12Q 1/56; G01N 33/86
[52] U.S. Cl. .................... 435/13; 435/810; 435/975; 436/69
[58] Field of Search .......... 435/13, 69.2, 69.6, 435/71.1, 74.226, 810, 968, 975; 436/69; 422/61

[56] References Cited

U.S. PATENT DOCUMENTS

| | | | |
|---|---|---|---|
| 5,001,069 | 3/1991 | Bartl | 436/86 |
| 5,051,357 | 9/1991 | Hassouna | 435/13 |
| 5,059,525 | 10/1991 | Bartl | 435/13 |
| 5,169,786 | 12/1992 | Carroll | 436/69 |
| 5,308,756 | 5/1994 | van de Waart et al. | 435/13 |

FOREIGN PATENT DOCUMENTS

| | | |
|---|---|---|
| 0434377 | 6/1991 | European Pat. Off. |
| 464135 | 3/1991 | Sweden . |
| WO9011368 | 10/1990 | WIPO . |
| 9101382 | 2/1991 | WIPO . |
| WO9101383 | 2/1991 | WIPO . |
| WO9102812 | 3/1991 | WIPO . |

OTHER PUBLICATIONS

Amer, L. et al., Impairment of the Protein C Anticoagulant Pathway in a Patient with Systemic Lupus Erythematosus, Anticardiolipin Antibodies and Thrombosis; Thrombosis Research 57; pp. 247-258, 1990.

Griffin, J. et al., Anticoagulant Protein C Pathway Defective in Majority of Thrombophilic Patients; Blood, vol. 82, No. 7 pp. 1989-1993, Oct. 1, 1993.

Thrombophilia: a new factor emerges from the mists; The Lancet, vol. 342, pp. 1501-1506, Dec. 18/25, 1993.

Faioni, E. M. et al., Resistance to Activated Protein C in Nine Thrombophilic Families: Interference in a Protein S Functional Assay; Thrombosis and Haemostasis, F. K. Schattauer Verlagsgesellschaft mbH (Stuttgart) 70 (6) 1067-1071 (1993).

Dahlback, B. et al., Inherited resistance to activated protein C is corrected by anticoagulant cofactor activity found to be a property of factor V; Proc. Natl. Acad. Sci. USA, vol. 91, pp. 1396-1400, Feb. 1994.

Bauer, Kenneth A., M.D., Hypercoagulability-A New Cofactor in the Protein C Anticoagulant Pathway; New England Journal of Medicine, vol. 330, pp. 566-567, Feb. 24, 1994.

Chromogenix, Coatest APC Resistance Kit Instructions May 1993.

Chromogenix, Coatest APC Resistance Kit Brochure Jun. 1993.

Chromogenix, Thrombophilia 1993-1994, Coatest APC-Resistance Brochure Oct. 1993.

Dahlback, B. et al.,Familial thrombophilia due to a previously unrecognized mechanism characterized by poor anticoagulant response to activated protein C: Prediction of a cofactor to activated protein C; Proc. Natl. Acad. Sci. USA, vol. 90, pp. 1004-1008, Feb. 1993.

Mitchell, C. et al., A Fatal Thrombotic Disorder Associated with an Acquired Inhibitor of Protein C; New England Journal of Medicine, vol. 317, No. 26, pp. 1638-1642, Dec. 24, 1987.

Thromb. Haemost. 65, Abstract 39, 658, 1991.

Takahashi H., Fast Functional Assay of Protein C . . . Clinica Chimica Acta 175 (1988) 217-226.

Vasse M., Protein C: Roen, A New Hereditary . . . Thrombosis Research 56: 387-398 1989.

Dahlback B., Factor VIII Defect Associated with . . . Thrombosis & Haemostasis 65 Abst 39 p. 658 Jul. 1991.

*Primary Examiner*—William H. Beisner
*Assistant Examiner*—Ralph Gitomer
*Attorney, Agent, or Firm*—Birch Stewart Kolasch & Birch

[57] ABSTRACT

The present invention is directed to a method of detecting APC resistance and a kit for use with the method.

22 Claims, No Drawings

METHOD FOR THE DIAGNOSIS OF BLOOD COAGULATION DISORDERS

The present invention concerns a novel method appropriate for screening and diagnosis of thromboembolic diseases, e.g. hereditary thrombophilia. The invention can also be used for determining the risk for thrombosis in pregnant individuals, individuals undergoing surgery, individuals taking anti-conception drugs etc.

The blood coagulation comprises a complex system of inter-linked proenzymes, enzymes and cofactors performing its role at the surfaces of activated platelets and endothelial cells. When the system is activated the ultimate result is the formation of a blood clot containing insoluble fibrin. The initiation and termination of fibrin formation is carefully regulated in normal homeostasis. In vitro, platelets and endothelial cell surfaces are usually substituted with suitable phospholipids. For the invention the relevant part of the coagulation system is described in PCT WO93/10261.

The important part for the invention relates to Protein C (=PC) and effects produced by action of activated Protein C (=APC) on the coagulation system. Protein C is a zymogen that in vitro may be activated by thrombin (=Factor $II_a$) alone, the combination thrombin-thrombomodulin, certain snake venoms, such as from *Akistrodon Contortrix Contortrix*, or purified Factor $X_a$. Activation of sample endogenous Protein C or addition of exogenously activated Protein C to a plasma sample will neutralise Factors $V_a$ and $VIII_a$ (degradation) and lead to prolonged times for blood coagulation in plasma samples of healthy individuals. Factors V and VIII are activated by small amounts of thrombin or Factor $X_a$. Protein S is a cofactor to Protein C.

Hereditary heterozygous deficiences in Protein C, Protein S and Antithrombin III (ATIII, a coagulation factor opposing coagulation) are found in approximately 10–15% of patients with diagnosed thromboembolic disease before the age of 40. Homozygous Protein C and S deficiencies are life threatening and affected individuals develop generalized microvascular thrombosis and purpura fulminance in the neonatal period.

Deficiencies in Protein C and S and ATIII are measured by both functional and immunological methods. One way of determining functional Protein C activity involves the steps: mixing the plasma sample to be tested with an excess of human plasma deficient in Protein C and addition of a Protein C activator and monitoring the appropriate substrate conversion. Highly specific assays have been achieved by using Protein C specific substrates. Alternatively one has also utilized substrates for enzymes, e.g. thrombin and Factor $X_a$, which activities are influenced by activated Protein C activity (i.e. enzyme activities that are generated or modulated by APC). In certain cases Protein C assays have involved isolation of the zymogen and a subsequent activation and addition of substrate to the activated form. Measurement of Protein C activity in plasma samples has also been suggested to be performed directly in the sample without addition of plasma deficient in Protein C. However, such methods will not discriminate an abnormality related to Protein C as such from a disorder related to factors interfering with the effects caused by Protein C (WO-A-91/02812).

Addition of activated Protein C to a plasma sample of a patient and study of the effect produced has been claimed to discover a defect Factor $VIII_a$ molecule that is not degraded by activated Protein C (B. Dahlbäck and M Carlsson, Thromb. Haemost. 65, Abstract 39, 658 (1991)). However, the data given in the present specification surprisingly indicate that the patient in question could not carry a defect Factor $VIII/VIII_a$.

In order to determine Protein S functional activity in a plasma sample the most common methods involve mixing the plasma sample with activated Protein C, an excess of Protein S deficient plasma and further reagents necessary to achieve clotting (Waart et al., Thromb. Res. 48, 427–37 (1987); Suzuki et al., Thromb. Res. 49, 241–51 (1988); Bertina et al., Thromb. Haemost. 53,268–72 (1985); and Comp et al., J. Clin. Invest. 74, 2084–88 (1984). It has also been suggested to measure Protein S by incubating the plasma sample with Factor $IX_a$ and activated Protein C and measurement of the clot time or the conversion of a chromogenic thrombin substrate (KabiVitrum AB (S. Rosen) WO-A-9101382).

The present inventor has realized that there are hitherto unrecognized thromboembolic disorders that can be diagnosed by the addition of activated Protein c to a patient sample containing coagulation Factors and measurement of an enzyme activity that is influenced by the APC added. The experimental results now presented indicate that the disorders in question are related to a hitherto unknown coagulation Factor(s) or unknown interactions of known Factors. The unknown Factor is not Factor $V_a$ or $VIII_a$ that are resistant to degradation by APC, or an inhibitor of the immunoglobulin-type for APC. The disorders are neither related to Protein S deficiency. For simplicity reasons the unknown Factor(s)/interaction(s) will be referred to as one unknown Factor in this text.

The samples assayed are normally plasma samples, but may also be other types of samples containing the coagulation factors in question. The invention will be illustrated in relation to plasma samples.

Accordingly the invention is an in vitro method for the diagnosis of a blood coagulation disorder in a human individual or for the determination of the risk for a human individual to acquire said blood coagulation disorder, said disorder possibly not being expressed by (1) Protein S deficiency, and optionally also by (2) forms of either Factor $V_a$ or Factor $VIII_a$ that are resistant to degradation by APC, or by (3) an inhibitor of the immunoglobulin type for APC. The characteristic feature of the method comprises the steps that:

(i) a plasma sample obtained from the individual is incubated with
  (a) an exogenous Reagent (I) activating at least partially the blood coagulation system of the sample, and with
  (b) activated exogenous Protein C (APC) or exogenous PC together with exogenous Reagents (II) that transform PC to APC, and
  (c) further components, such as $Ca^{2+}$ salt and phospholipid or tissue thromboplastin, that are necessary for efficient reaction of the activated factors introduced according to step (i:a), and
  (d) if desired, an exogenous substrate for an enzyme which activity is influenced by activated Protein C;

(ii) a substrate conversion rate is monitored directly for a blood coagulation enzyme which activity is influenced by activated Protein C, (iii) the conversion rate determined in step (ii) is compared with a standard value being obtained from steps (i)-(ii) under identical conditions for plasma of normal individuals.

In case the substrate conversion rate is not normal compared to the standard, the individual from which the sample derives is classified as suffering from the disorder or being at risk for acquiring the disorder. An increased conversion rate of the sample indicates a thromboembolic disease or a risk for such a disease (with fibrinogen as the substrate an increased conversion rate means a shortened clotting time). The significance of a lowered conversion rate is at the present stage not known (with fibrinogen as the substrate a lowered conversion rate means a prolonged clotting time). Probably it is not related to any disease.

The range of the normal conversion rate may be quite broad. Hence, it might, as a complement, be of value to run steps (i)-(ii) on a plasma sample from the individual with exclusion of the incubation according to (i:b) and compare the result obtained with that obtained according to the invention.

The incubation according to (i:a) serves to introduce an activated coagulation factor that can be used for the measurement in step (ii). The expression "partially" means that the addition of Reagent (I) leads to the presence of at least Factor $IX_a$. Reagent (I) may be a certain coagulation factor or a reagent that activates the system via the intrinsic or extrinsic pathway. Accordingly Reagent (I) may be Factor $IX_a$ or Factor $XI_a$ (intrinsic pathway), Factor $XII_a$ (intrinsic pathway), kallikrein (intrinsic pathway), a contact activator (intrinsic pathway) such as kaolin, celite or ellagic acid (intrinsic pathway), an APTT reagent (Activated Partial Thromboplastin Time; i.e. a reagent containing a phospholipid and a contact activator (intrinsic pathway), tissue thromboplastin (PT-reagent, PT=Prothrombin time, (extrinsic pathway)). In cases where a poor specificity is acceptable Reagent (I) may also be Factor $X_a$.

Protein C (i:b) may be of various species origin. In case the Protein C and the sample are of different species origin it is highly recommended to include Protein S (cofactor to activated Protein C) in the incubation mixture. Protein C and Protein S should be of the same species origin, for instance bovine Protein C requires bovine Protein S. Protein C is preferably activated prior to being added, although activation may also be accomplished after it has been added to the sample. Activation shall take place under standardised and defined conditions. Normal activation agents are those given on page 2. Recombinantly produced biologically functional forms of Proteins C and S can also be used.

The components used according to step i:c depend on the mode employed and may necessitate the inclusion of plasma protease inhibitors for enzymes other than the monitored one or of a fibrin polymerization inhibitor. $Ca^{2+}$ may be in the form of a plasma soluble salt that provides the $Ca^{2+}$ ion in free uncomplexed form, i.e. strong $Ca^{2+}$ chelators should be avoided. In the final assay medium the concentration of $Ca^{2+}$ may be selected within 0.5-50 mM, preferably within 5-15 mM, such as 6-7 mM. Too high a concentration may inhibit the coagulation system.

The substrate according to (i:d) is normally a synthetic substrate for an enzyme which activity is influenced by activated Protein C, e.g. thrombin (=Factor $II_a$) and Factor $X_a$. Suitable synthetic substrates are water soluble and have preferably oligopeptide structure with three, four or five amino acid residues and an amino terminal that is protected from being attacked by amino peptidases. The protection is accomplished either by a protecting group or by having a D-amino acid in the amino terminal. In order to give a detectable response the carboxy terminal of a synthetic substrate is amidated with a group that specifically can be released and detected upon action of the relevant blood coagulation protease. The group to be released is selected among chromogenic, fluorogenic or chemiluminogenic groups and other analytically detectable groups. See further H. C. Hemker, "Handbook of synthetic substrates for the coagulation and fibrinolytic system", Martinus Nijhoff Publishers, 1983, and J. Fareed et al, "Synthetic peptide substrates in hemostatic testing" in CRC Critical Reviews in Clinical Laboratory Sciencies Vol 19, Issue 2, 71-134(1983). In case of samples other than plasma samples exogenous fibrinogen may be added as substrate.

The order of addition and the incubation vary with the mode of the invention. For instance in case Reagent (I) is an APTT reagent (i:a) and the substrate conversion to be monitored is fibrinogen to fibrin, reagent (I) is added to the sample and allowed to maximally activate Factor XI to Factor $XI_a$. Then $Ca^{2+}$ (i:c) is added and the time for clotting measured. Activated Protein C according to step (i:b) is introduced either simultaneously with, prior to or after the activation to Factor $XI_a$. A PT-assay is performed similarly with addition of tissue thromboplastin (instead of the APTT reagent) to the sample in an amount sufficient for activation of Factor X to Factor $X_a$ or Factor IX to Factor $IX_a$. Thereafter activated Protein C (i:b) is added and finally the clotting time is measured as in any APTT assay. In case a synthetic substrate is used it can be added at any stage before or at the start of the monitoring reaction. In order to run the monitoring reaction with high specificity, the above-mentioned inhibitors may be introduced at any suitable stage into the reaction medium. For instance it may be appropriate to add a thrombin inhibitor together with a substrate for Factor $X_a$, when Factor $X_a$ activity is measured. The same inhibitor added prior to addition of the substrate may, however, adversely affect the formation of Factor $X_a$.

In order to accomplish a specific result with respect to the above-mentioned unknown Factor one should try to keep the patient plasma sample content of the final assay medium as high as possible. Accordingly patient plasma sample content in tests having good specificity should be >10 %, in particular >20% or >35% (v/v).

It may be practical to sell and use reagents according to (i:a-d) in predispensed combinations that may have been lyophilized separately or as mixtures containing at least two of the components given in (i:a-d), preferably in the doses used for testing. It may also be practical to have performed the lyophilization in the vial to be used in the assay. Suitable combinations are (concentration ranges refer to values during the assay, preferred ranges are given within brackets):

A. APTT based clot methods and APTT dependinq clot methods for factors V and VIII.

| 1. Human APC | 10 ng/mL-50 µg/mL |
| --- | --- |
| | (25 ng/mL-10 µg/mL) |
| 2. APC species (non-human) | 100 ng/mL-50 µg/mL |
| | (10 ng/mL-50 µg/mL) |
| 3. Bovine APC/Bovine Protein S, from other non-human species. | APC: 5 ng/mL-5 µg/mL Protein S: 100 ng/mL-20 µg/mL |

-continued (10 ng/mL–20 µg/mL)

All reagents given in 1–3 above and intended to be used in the invention may be lyophilized in the absence or presence of $Ca^{2+}$. If present, the amount of $Ca^{2+}$ should give a $Ca^{2+}$ concentration of 0.5–30mmol/L in the final assay medium. Phospholipid may be included in the lyophilized preparations.

B. APTT modified clot methods in which contact factor activation has been excluded.

| | |
|---|---|
| Factor $IX_a$ | 0.05 ng/mL–2 µg/mL |
| Factor $XI_a$ | 0.05 ng/mL–2 µg/mL |
| Factor $XII_a$ | 0.05 ng/mL–2 µg/mL |
| Kallikrein | 0.05 ng/mL–2 µg/mL |

No limitation regarding species. $FIX_a$ may also be used together with any of the combinations A 1–3 including the presence or absence of $Ca^{2+}$ and phospholipid.

C. APTT chromogenic methods.

Combinations according to A 1–3 with inclusion of fibrin polymerization inhibitor (concentration $>/=K_I$, $K_I$=inhibition constant) and chromogenic substrate (concentration $>/=0.1K_m$, $K_m$=Michaelis-Menten constant). Alternatively the chromogenic substrate is lyophilized separately or in the presence of $Ca^{2+}$ that in turn optionally is combined with a fibrin polymerization inhibitor. In a minor alternative the substrate is lyophilized together with a fibrin polymerization inhibitor but in the absence of $Ca^{2+}$. The constituents shall provide conditions such that no disturbing substrate hydrolysis takes place during reconstitution.

D. APTT modified chromogenic methods in which contact factor activation has been excluded.

Combinations of reagents as given under B and C.

E. PT clot method utilizing tissue thromboplastin.

Reagents according to A 1–3 optionally combined with $Ca^{2+}$ and/or tissue thromboplastin.

F. Modified clot method for screening of Factor V defect.

| | |
|---|---|
| Factor $X_a$ | 0.02 ng/mL–0.5 µg/mL |

Factor $X_a$ is not limited to species. The reagent may contain combinations according to A 1–3 optionally together with $Ca^{2+}$ and/or phospholipid.

G. PT chromoqenic method.

Combinations according to C and E above but with thromboplastin instead of phospholipid.

H. Chromogenic Factor VIII method.

Reagents according to A 1–3 employed in a standard chromogenic Factor VIII assay. The reagents may have been lyophilized together with either of Factor $IX_a+/-$$-Ca^{2+}+/-$ phospholipid or Factor $X+/-Ca^{2+}+/-$ phospholipid, with Factor X concentration of 0.1/ug/mL–50/ug/mL. The reagent may also comprise inclusion of small amounts of thrombin and, when Factor X is included, also Factor $IX_a$. Furthermore, a chromogenic substrate for Factor $X_a$ may be included in the reagent.

I. Chromogenic Factor V method.

Reagents according to C and F with or without inclusion of prothrombin (0.02 ng/mL–50/ug/mL)

APTT reagents may be included in combinations A–D, provided they are not co-lyophilized with $Ca^{2+}$. Active enzymes and their substrates may be co-lyophilized as recently described (EP-A-318,571).

The invention is primarily intended as a screening method in order to find individuals that need further diagnosis, but comprises also specific factor assays according to F, H and I above. The proper selection of reagent (I) and substrate to be monitored (i:d) refine the possibility of finding where in the coagulation system a diagnosed disorder is located. In principle the inventive method will detect disorders related to defective interactions between activated Protein C and Factor $V_a$, Factor $VIII_a$. It will also detect the presence of inhibitors of activated Protein C, and abnormalties in hitherto unrecognized interactions and factors influenced by Protein C activation or activated Protein C activity.

The invention will now be illustrated by way of the inventors discovery of a patient suffering from a novel disorder in the blood coagulation system. The appending claims are an integral part of the description.

EXPERIMENTAL PART

Case Report:

The proband is a male born in 1942. In 1961, he had the first episode of deep venous thrombosis in one of the legs. After this, he was healthy and free of thrombosis for almost 20 years. Between 1980 and 1987 he had multiple thrombotic episodes, occurring at least once a year. The thrombotic events were treated with vitamin K antagonists for up to three months. A thrombus was positively verified with flebography at least at two occasions. The proband has developed a post-thrombotic syndrome in his legs. He has no other disorders. In 1987, he quit smoking and at the same time he started taking aspirin daily. During 1987–1991 he has not experienced any thrombo-embolic episode. Both male and female members of the patient's family have similar histories with multiple episodes of deep venous thrombosis. His 10 year older brother have had deep venous thrombosis at multiple occasions, most of them occurring between the age of 45 and 50. The proband also reports that an uncle on his mother's side has had a medical record with multiple episodes of thrombosis. The patient's mother was born in 1905, and she has had episodes when deep venous thrombosis has been suspected clinically. Two more brothers and a sister have had incidences where thrombosis has been suspected.

Known coagulation and immunological methods used as a complement to the inventive method for the diagnosis.

The activated partial thromboplastin time (APTT, Organon Technica), Owren's P&P, thrombin time and reptilase time were determined with standard methods.- .Antithrombin III was measured with an amidolytic assay (Coatest ATIII, Kabi Diagnostica, Molndal, Sweden). Total and free Protein S and Protein C antigen levels were determined with previously described immunochemical methods (Malm J. et al., *Br. J. Haemat.* 68, 437–443 (1988). Protein C function activity was analysed with a synthetic substrate after activation with the venom from *Agkistrodon Contortrix Contortrix* using a commercially available kit (Coatest Protein C, Kabi Diagnostica AB, Molndal, Sweden).

Absorption of IgA, IgG and IgM was performed as previously described (Dahlbäck B. et al., Blood 62, 218–225 (1983).

A second functional Protein C assay was also performed as previously described (Hickton C. M., Thromb. Res. 41 501–8, (1986)). The method included barium-citrate absorption of plasma. The proteins that bound to the barium-citrate were eluted and the eluate was incubated with a thrombin-thrombomodulin complex to activite Protein C. The amount of APC after activation was quantified using an APTT clotting assay.

Inventive methods

1. An APTT based method was used to determine the anticoagulant effect of purified APC in patient plasma. In this method (APC-APTT assay) the APC mediated prolongation of the APT-time was measured as follows: 0.1 ml plasma was incubated with 0.1 ml APTT reagent for 5 minutes at 37° C. before addition of 0.1 ml of an APC-$Ca^{2+}$ mixture (0–20/ug/ml APC in 10 mM Tris-HCl, 0.15 M NaCl, 30 mM calcium chloride pH 7.5 containing 0.1% bovine serum albumin (BSA)) which initiated blood coagulation. The APC was prepared as previously described (Dahlbäck B. et al., J. Biol. Chem. 261, 12022–12027 (1986). The assay was run with bovine APC with or without the presence of bovine Protein S.

Normally APTT assays are run without addition of NaCl. Accordingly, but also because NaCl prolongs the coagulation times, it is preferred to run this mode of the invention without addition of NaCl.

2. In order to determine the effect of APC on plasma Factor V, increasing concentrations of APC (10/ul diluted in 10 mM Tris-HCl, 0.15 M NaCl, pH 7.5 containing 0.1% BSA) were added to 0.09 ml plasma. Immediately after the APC-addition, 0.1 ml rabbit brain cephalin (diluted in 0.15 M NaCl) and 0.1 mL 30 mM $CaCl_2$ were added. After incubation for 15 seconds at 37° C., clotting was initiated with 0.1 ml Factor $X_a$ (150 ng/ml diluted in 10 mM Tris-HCl, 0.15 M NaCl, pH 7.5 containing 0.1% BSA). In the absence of APC, this Factor $X_a$ concentration gave an approximate clotting time of 30 seconds in the control plasma used. Factor $X_a$ was prepared as described previously (Dahlbäck B. et al., J. Biol. Chem. 261, 12022–12027 (1986)).

3. A modification of a commercial Factor VIII assay (Coatest Factor VIII, Kabi Diagnostica AB, Molndal, Sweden) was used to analyse the effect of APC on plasma Factor VIII. Patient or control plasma (25/ul 1/125 to 1/400 in 10 mM Tris-HCl, 0.15 M NaCl, pH 7.5 containing 0.1% BSA) was incubated with 75/ul of the kit reagent containing Factor $IX_a$, Factor X, phospholipid and $Ca^{2+}$. Just prior to the test, increasing concentrations of APC (0.1–100/ug/ml) were added to this reagent. After 20 minutes incubation at 37° C., 50/ul of a mixture of the synthetic substrate (2.7 nM) (Bz-Ile-Glu(gamma-OR)-Gly-Arg-pNA=S-2222, Kabi Diagnostica, Molndal, Sweden) and the thrombin inhibitor (60/uM) (N-dansyl-(p-guanidino)-Phe-piperidide=I-2581, Kabi Diagnostica AB, Mändal, Sweden) was added. After incubation for 10 minutes more at 37° C., the reaction was interrupted by the addition of 150/ul (1 M) citric acid and the absorbance was measured at 405 nm. A standard curve for Factor VIII was made using normal plasma diluted from 1/100 to 1/800.

Results of the methods used in the cause of the investigation.

The APT-time together with values for ATIII and Protein S were normal and the patient had no indications of the presence of lupus anticoagulants. The plasma level of Protein C was normal, both when being measured with the immunological method and with the functional assay, which included Protein C activation with snake venom and quantitation of APC with a synthetic substrate.

The barium-citrate functional Protein C assay gave consistently lower Protein C values for the eluate when diluted 1:10 compared to 1:40. This might indicate the presence of an inhibitor for APC. In order to check this, we used the inventive APC-APTT assay. The clotting time obtained was always shorter than for the control plasma. In order to rule out an inhibitor of the immunoglobulin type, the patient's plasma was depleted completely in IgA, IgG or IgM by absorption. The shortened clotting time did not disappear. The results found could be due to a functional Protein S deficiency. However, this possibility was ruled out since bovine APC, when added with or without bovine Protein S is considerably less efficient in prolonging the APT-time of the proband's plasma compared to prolongation in the control plasma.

A third possible mechanism for the observed APC-resistance was that the proband's Factor $V_a$ or Factor $VIII_a$ could be resistant to cleavage by APC. To elucidate this possibility, assays were devised which directly measured the inhibition of plasma factors $V_a$ and $VIII_a$ by APC. Using the Factor $X_a$ based clotting assay (described above), the inhibition of patient Factor $V_a$ by APC was found to be normal suggesting that Factor $V_a$ in the patient's plasma was degraded in a normal fashion by exogenously added APC. This experiment ruled out the possibility of a Protein C inhibitory antibody explaining the APC-resistance. To test the remaining possibility, i.e. that APC could not degrade the proband's Factor $VIII_a$, the effect of added APC in a Factor $VIII_a$ assay was tested. However, the proband's Factor $VIII_a$ was found to be normally degraded by the added APC when compared to control plasma. This finding is contrary to the inventor's earlier publication (B. Dahlbäck and M Carlsson, Thromb. Haemost. 65, Abstract 39, 658 (1991)).

To investigate whether the APC-effect was inherited, 18 family members were analyzed using the APC-APTT assay. 10 (both male and female) of the 18 tested family members did not respond to APC with normal prolongation of their clotting times, which suggests that the factor molecule responsible for the effect is resistant to APC. This result shows that the defect molecule was inherited and present in the family members that did not give normal prolongation of their clotting times. It is noteworthy that in the absence of added APC, the APT-times of these individuals and of the proband were shorter than for the controls. This may suggest partial degradation of relevant Factor molecules during APTT assays of normal plasma. To test the sensitivity of the APC-APTT assay for the presence of APC-resistance, mixtures of proband and normal plasma (1:1, 1:10 and 1:100) were analyzed. When added to the 1:1 mixture, APC was equally inefficient in prolonging the clotting time as when added to the proband's plasma. Half of the normal prolongation was observed when testing the 1:10 mixture, whereas the 1:100 mixture behaved like control plasma. Thus the APC-APTT assay did not discriminate between the presence of 50% and 100% APC resistant factor molecules suggesting the method to be a useful screening method for the identification of carrier states.

Since the measured lack of substantial prolongation of the clotting time is not related to Factors $VIII_a$ and $V_a$ or a Protein C inhibitor of the immunoglobulin type or a defective Protein S-APC interaction the effect is likely to be associated with a hitherto unrecognized coagulation factor.

The APC-APTT assay according to the invention has also been run on plasma samples from about 100 patients with diagnosed thrombosis. About 10% of the patients gave shortening of their clotting times compared to the standard. No apparent heredity could be seen. None of the patients had been found positive in other assays for the determination of coagulation disorders.

An APC-APTT method similar to method 1 under the heading Inventive Methods 1 given above has been run on plasma samples from Protein S deficient patients. In this specific mode the APC amount was adjusted so that pooled normal plasmas resulted in a prolongation of the coagulation time of 40 seconds. The new type of patients we have detected then gave a prolongation of coagulation time of 0-15 seconds while plasma from patients with diagnosed Protein S deficiency gave a prolongation time that was close to normal. In order to check further the influence of Protein S deficiency we also assayed normal plasma that had been made deficient in Protein S by immune adsorption. The prolongation time decreased with about 50% which indicates that the prolongation measured for our new patient group is not caused by Protein S deficiency. We have also added Protein S to plasma from the new patient group and run the inventive method on such plasma. The result has been that the prolongation of the coagulation time is not normalised which further supports that the inventive method does not measure Protein S.

By varying the plasma content of the assay medium it was experimentally verified that one should avoid too low plasma concentrations in the final assay medium.

Restriction digestion of DNA, PCR and hybridization for assaying a Factor VIII gene X-linked inheritance of the disorder.

DNA from three relatives (the proband, his mother and one of his brothers) that were suspected of carrying a gene for the disorder was subjected to PCR with amplification of the Factor VIII gene and subsequent cleavage with Bcl 1 as described previously (Kogan et al., *N. Engl. J. Med.* 317, 985-90 (1987)).

In the human population this treatment leads to two different fragments (1.42 kb and 91 kb, respectively). The DNA of an individual will carry genes giving either both fragments or only one fragment. The mother's DNA gave both 142 kb and 91 kb fragments, while one of her sons gave only the 142 kb fragment and the other only the 91 kb fragment. This is a clear indication that the two sons have received different Factor VIII genes from their mother. The disorder traced could thus not be linked to a gene on an X-chromosome.

I claim:

1. An in vitro method for screening and diagnosing activated protein C (APC) resistance which is recognized by a low anti-coagulant response to exogenous activated Protein C (APC) not related to Protein S deficiency or defective $FVIII/FVIII_a$ and recognized by a low anti-coagulant response to exogenous activated Protein C (APC) in the absence of APC immunoglobulin inhibitors said method comprising the steps of:

(i) incubating a human plasma sample from a human in need of screening and diagnosing for APC resistance with (1) exogenous APC, or exogenous Protein C and an exogenous reagent that transforms exogenous Protein C to APC;

(2) an exogenous reagent (I) which at least partially activates a coagulation factor of the blood coagulation system of said human plasma sample; and optionally (3) an exogenous substrate for an enzyme wherein the activity of said enzyme is influenced by APC, to prepare a final assay medium;

(ii) measuring a substrate conversion rate for a coagulation factor directly or indirectly activated in step (i), the activity of which is influenced by APC; and (iii) comparing said substrate conversion rate measured in step (ii) with a standard value obtained from samples of normal individuals, said samples of normal individuals having been subjected to steps (i) and (ii)

wherein when said substrate conversion rate obtained for said human plasma sample in step (ii) is higher than the standard value, said human has APC resistance.

2. The method of claim 1, wherein the final assay medium has a plasma sample content of at least 10% (v/v).

3. The method of claim 1, wherein reagent (I) is an activated partial thromboplastin time (APTT) reagent comprising a phospholipid or phospholipids and a contact activator.

4. The method of claim 1, wherein the plasma sample is incubated with the components of (i)(1), and, optionally, (i)(3) after a preincubation of the sample with exogenous reagent (I) for a time sufficient to activate the blood coagulation system of the sample.

5. The method of claim 1, wherein said exogenous APC of (i)(1) comprises purified human APC.

6. The method of claim 1, wherein the exogenous APC of (i)(1) comprises bovine APC.

7. The method of claim 1, wherein the plasma sample is incubated in step (i) with exogenous human Protein C or non-human Protein C, optionally together with a Protein S derived from the same species as Protein C.

8. The method of claim 1, wherein in step (ii), the conversion of fibrinogen to fibrin is measured.

9. The method of claim 1, wherein said exogenous reagent (I) is (a) components necessary to activate the blood coagulation system of the sample via the intrinsic pathway, or (b) components necessary to activate the blood coagulation system via the extrinsic pathway, or (c) components necessary to activate the blood coagulation system of the sample via the intrinsic pathway and components necessary to activate the blood coagulation system via the extrinsic pathway and components (i)(1), and (i)(3) are added simultaneously with, or after exogenous reagent (I) has been allowed to incubate with the sample for a sufficient time to activate the intrinsic pathway, or the extrinsic pathway, or the intrinsic and the extrinsic pathways.

10. The method according to claims 1 or 9, wherein said exogenous substrate is present and optionally a fibrin polymerization inhibitor is added, and substrate conversion is measured.

11. The method according to claim 10, wherein said exogenous substrate is specific for $X_a$ and is optionally present together with a fibrin polymerization inhibitor.

12. The method according to claim 10, wherein said exogenous substrate is specific for thrombin and is optionally present with a fibrin polymerization inhibitor.

13. The method according to claims 1 or 9, further adding a fibrin polymerization inhibitor, and said exogenous substrate being a synthetic peptide, said synthetic peptide comprising a group that is specifically released and becomes analytically detectable upon action of an enzyme, said group being bound in an amide linkage to the carboxy terminal of the peptide and being selected from a chromogenic, fluorogenic or chemiluminogenic group.

14. The method according to claims 1 or 9, wherein at least one of components of (i)(1)-(i)(3) are lyophilized components, and including a step of reconstituting said lyophilized components prior to step (i).

15. The method according to claim 1, wherein said exogenous reagent (I) is exogenous Factor $X_a$ or exogenous Factor $IX_a$, optionally, in combination with exogenous prothrombin.

16. The method according to claim 1, wherein said exogenous reagent (I) is exogenous Factor X in combination with exogenous Factor $IX_a$, or a combination of Factor X, Factor $IX_a$ and thrombin.

17. The method of claim 1, further comprising comparing the substrate conversion rate measured for the plasma sample in step (ii) with a second substrate conversion rate obtained for a second plasma sample derived from said human, wherein said second plasma sample has been subjected to steps (i) and (ii) under the same conditions as the first plasma sample but in absence of component (i) (1).

18. The method according to claim 1, wherein said exogenous reagent (I) comprises $FIX_a$ or FX, and said exogenous substrate is a chromogenic substrate for $FX_a$.

19. The method according to claim 1, wherein said exogenous reagent (I) comprises $FX_a$, and said exogenous substrate is a chromogenic thrombin substrate.

20. An activated protein APC resistance test kit comprising components (i) (1)-(i)(3) as described in claim 1 in separate containers, or as mixtures of at least two of said components in each container.

21. The test kit according to claim 20, wherein said components are lyophilized.

22. The test kit according to claim 20 comprising in one container an activated partial thromboplastin time (APTT) reagent comprising phospholipids and a contact activator, and in a second container APC and a calcium source.

* * * * *

REEXAMINATION CERTIFICATE (3704th)

United States Patent [19]

Dahlbäck

[11] B1 5,443,960

[45] Certificate Issued Jan. 12, 1999

[54] METHOD FOR THE DIAGNOSIS OF BLOOD COAGULATION DISORDERS

[75] Inventor: Björn Dahlbäck, Malmö, Sweden

[73] Assignee: T.A.C. Thrombosis and Coagulation AB, Malmö, Sweden

Reexamination Request:
No. 90/004,865, Dec. 10, 1997

Reexamination Certificate for:
Patent No.: 5,443,960
Issued: Aug. 22, 1995
Appl. No.: 199,328
Filed: May 27, 1994

[22] PCT Filed: May 13, 1992
[86] PCT No.: PCT/SE92/00310
§ 371 Date: May 27, 1994
§ 102(e) Date: May 27, 1994
[87] PCT Pub. No.: WO93/10261
PCT Pub. Date: May 27, 1993

[30] Foreign Application Priority Data

Nov. 13, 1991 [SE] Sweden .................. 9103332-4

[51] Int. Cl.$^6$ .................. C12Q 1/56; G01N 33/86
[52] U.S. Cl. .................. 435/13; 435/810; 435/975; 436/69
[58] Field of Search .................. 435/13, 69.2, 69.6, 435/71.1, 810, 968, 975; 436/69; 422/61

[56] References Cited

U.S. PATENT DOCUMENTS 5,051,357 9/1991 Hassouna .................. 435/13
5,506,112 4/1996 Lang et al. .................. 435/13

FOREIGN PATENT DOCUMENTS 9102812 3/1991 WIPO.

OTHER PUBLICATIONS

Kisiel, et al., "Proteolytic Activation of Protein C . . . ", Biochem 15:4893-4900 (1976).
Seegers, et al., "Relationship of New Vitamin K-Dependent . . . ", Thromb. Res.8:543-552 (1976).
Kisiel, et al., "Anticoagulant Properties of Bovine Plasma Protein C . . . ", Biochem 16:5824-5831 (1977).
Kisiel, J. Clin. Invest., "Human Plasma Protein C: . . . ", 64:761-769 (1979).
Walker, et al., "The Inhibition of Blood Coagulation by . . . ", Biochim. Biophys. Acta 571:333-342 (1979).
Suzuki, et al., "Inactivation of Human Coagulation . . . ", 258:1914-1920 (1983).
Walker, J., "Regulation of Activated Protein C . . . ", Biol. Chem. 255:5521-5524 (1980).
DiScipio, et al., "A Comparison of Human Prothrombin, . . . ", Biochem 16:698-704 (1977).
Walker, et al., "Inactivation of Factor VIII By Activated . . . ", Biophys. 252:322-328 (1987).
Solymoss, et al., "Kinetics of Inactivation of Membrane-bound . . . ", J.Biol.Chem. 263:14884-14890 (1988).
Kane and Davie, "Blood Coagulation Factors V and VII: . . . ", Blood 71 (3) 539-555 (1988).
Walker and Fay, "Regulation of Blood Coagulation . . . ", FASEB J. 6: 2561-2567. 1992.
Aparicio and Dahlback, Biochem. J. 313: 467-472 (1996).
Amer, et al., Thromb. Res. 57: 247-258 (1990).
Walker, Thromb. Res. 22: 321-327 (1981).
Walker, F., Semin. Thromb. Haemost. 10: 131-138 (1984).
Stenflo, Semin. Thromb. Haemost. 10: 109-121 (1984).
Dahlback, B. & M. Carlsson, Thromb. Haemost. 65, Abstract 39, (1991).
Dahlback, et al., Proc. Nat. Acad. Aci. USA 90: 1004-1008 (1993).
Mitchell, et al., N. Engl. J. Med. 317 (26): 1638-1642 (1987).
Svensson, et al., Thromb. Haemost. 77: 332-335 (1997).
Cadroy, et al., Thromb. Haemost. 73: 734-735 (1995).
Giddings JC, In: Ruggeri ZM, editor. London: W.B. Saunders, pp. 571-596. (1985).
Marciniak, Science 170: 452-453 (1970).
Laudano and Doolittle, Proc. Natl. Acad. Sci. USA 75: 3085-3089 (1978).
Laudano, AP, Doolittle, RF, Biochemistry 19: 1013-1019 (1980).
Laudano, et al., Ann NY Acad. Sci Sci. 408: 315-329 (1983).
Root-Bernstein and Westall, Proc. Natl. Acad. Sci. USA 81: 4339-4342 (1984).
Miletich, et al., New Eng. J. Med. 317: 991-996 (1987).
Shen and Dahlback, J. Biol. Chem. 269: 18735-18738 (1994).
Varadi, et al., Thromb. Haemost. 73: 730-731 (1995).
Varadi, et al., Brit. J. Haematol. 90: 884-891 (1995).
Salem, et al., Proc. Nat. Acad. Sci. USA 80: 1584-1588 (1983).
Dahlback and Stenflo, Haemostasis and Thromb. 3rd Ed. Bloom, Ch. 30, pp. 671-698 (1994).
Pratt, C.W., et al., Thrombos. Res. 53: 595-602 (1989).
Bertina, R.M., et al., Nature 369: 64-67 (1994).
Dahlback, B., Scand. J. Clin. Lab. invest. Suppl. 191: 47-61 (1988).
Dahlback, B., J. Intern. Med. 237: 221-227 (1995).
Dahlback, B., Thromb. Res. 77: 1-43 (1995).
Dahlback, B., Thromb. Haemost. 74: 139-148 (1995).
Dahlback, B., et al., Proc. Natl. Acad. Sci. USA 91: 1396-1400 (1994).
Dahlback, B., et al., Ann. Hematol. 72: 166-176 (1996).
Esmon, C.T., Blood 62: 1155-1158 (1983).
Esmon, C.T., Science 235: 1348-1352 (1987).
Esmon, C.T., J. Biol. Chem. 264: 4743-4746 (1989).
Griffin, J.H., et al., Thromb. Haemost. 74: 444-448 (1995).
Heeb, J.J., et al., Blood 85: 3405-3411 (1995).
Jackson, D.E., et al., Thromb. Haemost. 72: 70-73 (1994).

(List continued on next page.)

*Primary Examiner*—Ralph Gitomer

[57] ABSTRACT

The present invention is directed to a method of detecting APC resistance and a kit for use with the method.

OTHER PUBLICATIONS

Kalafatis, M.R., et al., J. Biol. Chem. 270: 4053–4057 (1995).

Kalafatis, M.P., et al., Blood 87: 4695–4707 (1996).

Kalafatis, J., et al., J. Biol. Chem. 268: 27246–27257 (1993).

Kalafatis, M., et al., J. Biol. Chem. 269: 31869–31880 (1994).

Nicolaes, G.A., et al., J. Bio. Chem. 270: 21158–21166 (1995).

Rosing, J., et al., J. Biol. Chem. 270: 27852–27858 (1995).

Sun, X., et al., Blood 83: 3120–3125 (1994).

Svensson, P.J., et al., N. eng. J. Med. 330: 517–522 (1994).

Tuddenham, E.G., Lancet 343: 1515–1516 (1994).

Voorberg, J., et al., Lancet 343: 1535–1536 (1994).

Zoller, B., et al., Lancet 343: 1536–1538 (1994).

Zoller, B., et al., Thromb. Res. 85: 237–243 (1997).

Zoller, B., et al., Thromb. Haemost. 75: 270–274 (1996).

Zoller, B., et al., J. Clin. Invest. 94: 2521–2524 (1994).

Ireland, H., et al., Thromb. Haemost. 73: 731–732 1994.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–22 is confirmed.

* * * * *